United States Patent

Kaplan et al.

[11] Patent Number: 5,226,912
[45] Date of Patent: Jul. 13, 1993

[54] COMBINED SURGICAL NEEDLE-BRAIDED SUTURE DEVICE

[75] Inventors: Donald S. Kaplan, Weston; Matthew E. Hermes, Easton; Ross R. Muth, Brookfield; Herbert W. Korthoff, Westport, all of Conn.

[73] Assignee: United States Surgical Corporation, Norwalk, Conn.

[21] Appl. No.: 570,344

[22] Filed: Aug. 21, 1990

Related U.S. Application Data

[63] Continuation-in-part of Ser. No. 491,215, Mar. 9, 1990, Pat. No. 5,019,093, Ser. No. 529,740, May 22, 1990, Pat. No. 5,037,429, Ser. No. 221,308, Jul. 13, 1988, abandoned, Ser. No. 395,476, Aug. 18, 1989, abandoned, Ser. No. 413,240, Sep. 27, 1989, abandoned, Ser. No. 89,733, Aug. 26, 1987, abandoned, and Ser. No. 393,017, Aug. 10, 1989, abandoned, which is a continuation of Ser. No. 89,734, Aug. 26, 1987, abandoned, said Ser. No. 491,215, is a continuation of Ser. No. 344,745, Apr. 18, 1989, abandoned, which is a continuation-in-part of Ser. No. 227,699, Aug. 3, 1988, abandoned, which is a continuation-in-part of Ser. No. 89,732, Aug. 26, 1987, abandoned, said Ser. No. 529,740, is a continuation of Ser. No. 89,735, Aug. 26, 1987, abandoned.

[51] Int. Cl.⁵ ............................................. A61B 17/00
[52] U.S. Cl. ..................................... 606/224; 606/225; 606/227
[58] Field of Search ............................. 606/228–231, 606/224–227; 87/7; 428/224; 138/123; 139/317

[56] References Cited

U.S. PATENT DOCUMENTS

| | | |
|---|---|---|
| Re. 28,281 | 11/1965 | Bridgeford . |
| 86,769 | 2/1869 | Marriott . |
| 295,612 | 3/1884 | Bailey . |
| 299,305 | 5/1884 | Weed . |
| 877,476 | 1/1908 | Bach . |
| 1,106,667 | 8/1914 | Minahan . |
| 1,250,114 | 12/1917 | Bigelow et al. . |
| 1,558,037 | 10/1925 | Morton . |
| 1,591,021 | 7/1926 | Davis . |
| 1,613,206 | 1/1927 | Souttar . |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. . |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,917,410 | 12/1959 | Vitalls . |
| 2,928,395 | 3/1960 | Forbes et al. . |
| 3,009,893 | 11/1961 | Barnes et al. . |
| 3,125,095 | 3/1964 | Kaufman et al. . |
| 3,187,752 | 6/1965 | Glick . |
| 3,297,033 | 1/1967 | Schmitt et al. . |
| 3,311,110 | 3/1967 | Singerman et al. . |
| 3,359,983 | 12/1967 | Northey . |
| 3,371,069 | 2/1968 | Miyamae et al. . |
| 3,394,704 | 7/1968 | Dery . |
| 3,413,079 | 11/1968 | Rich, Jr. . |
| 3,416,534 | 12/1968 | Quinn . |
| 3,565,077 | 2/1971 | Glick . |
| 3,626,948 | 12/1971 | Glick et al. . |

(List continued on next page.)

*Primary Examiner*—Stephen C. Pellegrino
*Assistant Examiner*—Gary Jackson
*Attorney, Agent, or Firm*—Thomas R. Bremer; Peter G. Dilworth; Rocco S. Barrese

[57] ABSTRACT

A surgical needle is attached to a braided suture of particular construction to provide a combined surgical needle-braided suture device. A shrinkable tubing is employed to secure the needle to the suture. The tubing shrinks in response to the application of energy, e.g., heat. Attachment parameters may be controlled to provide standard needle attachment or removable needle attachment.

46 Claims, 7 Drawing Sheets

U.S. PATENT DOCUMENTS

| | | |
|---|---|---|
| 3,636,956 | 1/1972 | Schneider . |
| 3,655,927 | 4/1972 | Samuelson et al. . |
| 3,728,839 | 4/1973 | Glick . |
| 3,772,420 | 11/1973 | Glick et al. . |
| 3,799,169 | 3/1974 | Beroff et al. . |
| 3,835,912 | 9/1974 | Kristensen et al. . |
| 3,839,500 | 10/1974 | Dexter . |
| 3,839,524 | 10/1974 | Adams et al. . |
| 3,849,185 | 11/1974 | Shepherd et al. . |
| 3,875,946 | 4/1975 | Duncan . |
| 3,880,167 | 4/1975 | Hardwick . |
| 3,883,497 | 5/1975 | Gregory et al. . |
| 3,890,975 | 6/1975 | McGregor . |
| 3,896,814 | 7/1975 | Vivien et al. . |
| 3,910,282 | 10/1975 | Messer et al. . |
| 3,917,740 | 11/1975 | Siclari et al. . |
| 3,917,824 | 11/1975 | Camble et al. . |
| 3,918,455 | 11/1975 | Coplan . |
| 3,924,630 | 12/1975 | Walldorf . |
| 3,926,194 | 12/1975 | Greenberg et al. . |
| 3,942,532 | 3/1976 | Hunter et al. . |
| 3,943,933 | 3/1976 | Gertzman . |
| 3,948,875 | 4/1976 | Cohen et al. . |
| 3,949,755 | 4/1976 | Vauquois . |
| 3,949,756 | 4/1976 | Ace . |
| 3,963,031 | 6/1976 | Hunter . |
| 3,980,177 | 9/1976 | McGregor . |
| 3,981,307 | 9/1976 | Borvsko . |
| 3,991,766 | 11/1976 | Schmitt et al. . |
| 4,013,773 | 3/1977 | Murakami et al. . |
| 4,014,433 | 3/1977 | Cerwin . |
| 4,014,973 | 3/1977 | Thompson . |
| 4,024,871 | 5/1977 | Stephenson . |
| 4,027,676 | 6/1977 | Mattei . |
| 4,043,344 | 8/1977 | Landi et al. . |
| 4,047,533 | 9/1977 | Perciaccante et al. . |
| 4,052,988 | 10/1977 | Doddi et al. . |
| 4,054,144 | 10/1977 | Hoffman et al. . |
| 4,072,041 | 2/1978 | Hofffman et al. . |
| 4,080,969 | 3/1978 | Casey et al. . |
| 4,081,493 | 3/1978 | Kazama et al. . |
| 4,105,034 | 9/1978 | Shalaby et al. . |
| 4,124,027 | 11/1978 | Boss . |
| 4,126,428 | 11/1978 | Rude . |
| 4,127,133 | 11/1978 | Martinez . |
| 4,135,622 | 1/1979 | Glick . |
| 4,141,087 | 2/1979 | Shalaby et al. . |
| 4,157,085 | 6/1979 | Austad . |
| 4,162,242 | 7/1979 | House . |
| 4,169,477 | 10/1979 | Bokros . |
| 4,179,337 | 12/1979 | Davis et al. . |
| 4,185,637 | 1/1980 | Mattei . |
| 4,201,216 | 5/1980 | Mattei . |
| 4,204,542 | 5/1980 | Bokros et al. . |
| 4,206,101 | 6/1980 | Wysong . |
| 4,321,038 | 3/1982 | Porteous . |
| 4,330,338 | 5/1982 | Banker . |
| 4,359,053 | 11/1982 | Benjamin . |
| 4,362,162 | 12/1982 | Nakajima et al. . |
| 4,363,319 | 12/1982 | Altshuler . |
| 4,411,654 | 10/1983 | Boarini et al. . |
| 4,412,986 | 11/1983 | Kawata et al. . |
| 4,432,964 | 2/1984 | Shell et al. . |
| 4,439,181 | 3/1984 | Blackshear et al. . |
| 4,444,927 | 4/1984 | Borysko . |
| 4,452,973 | 6/1984 | Casey et al. . |
| 4,466,431 | 8/1984 | Tharrat et al. . |
| 4,469,837 | 9/1984 | Cattaneo . |
| 4,523,591 | 6/1985 | Kaplan et al. . |
| 4,528,186 | 7/1985 | Nishimura et al. . |
| 4,532,929 | 8/1985 | Mattei et al. . |
| 4,546,769 | 10/1985 | Planck et al. . |
| 4,579,731 | 4/1986 | Fox, Jr. et al. . |
| 4,588,400 | 5/1986 | Ring et al. . |
| 4,594,240 | 6/1986 | Kawata et al. . |
| 4,596,728 | 6/1986 | Yang et al. . |
| 4,600,743 | 7/1986 | Shizuki et al. . |
| 4,620,974 | 11/1986 | Hersch et al. . |
| 4,621,052 | 11/1986 | Sugimoto . |
| 4,621,638 | 11/1986 | Silvestrini . |
| 4,624,256 | 11/1986 | Messier et al. . |
| 4,624,879 | 11/1986 | Van Dijck et al. . |
| 4,649,920 | 3/1987 | Rhum . |
| 4,653,497 | 3/1987 | Bezwada et al. . |
| 4,672,734 | 6/1987 | Kawada et al. . |
| 4,705,820 | 11/1987 | Wang et al. . |
| 4,711,241 | 12/1987 | Lehmann . |
| 4,717,717 | 1/1988 | Finkenaur . |
| 4,742,003 | 5/1988 | Derynck et al. . |
| 4,743,679 | 5/1988 | Cohen et al. . |
| 4,775,501 | 10/1988 | Rosenzweig et al. ............... 264/27 |
| 4,792,336 | 12/1988 | Hlavacek et al. . |
| 4,801,456 | 1/1989 | Drengler . |
| 4,805,292 | 2/1989 | Noguchi . |
| 4,806,621 | 2/1989 | Kohn et al. . |
| 4,857,602 | 8/1989 | Casey et al. . |
| 4,861,757 | 8/1989 | Antoniades et al. . |
| 4,874,746 | 10/1989 | Antoniades et al. . |
| 4,906,474 | 3/1990 | Langer et al. . |
| 4,911,908 | 3/1990 | Estis et al. . |
| 4,913,903 | 4/1990 | Sudmann et al. . |
| 4,917,685 | 4/1990 | Viswanathan et al. . |
| 4,926,860 | 5/1992 | Stice et al. ......................... 606/144 |
| 4,929,242 | 5/1990 | Powell . |
| 4,944,948 | 7/1990 | Uster et al. . |
| 5,019,093 | 5/1991 | Kaplan et al. ....................... 606/228 |

FOREIGN PATENT DOCUMENTS

| | | |
|---|---|---|
| 0358451 | 3/1980 | European Pat. Off. . |
| 0046039 | 2/1982 | European Pat. Off. . |
| 0128733 | 12/1984 | European Pat. Off. . |
| 0131868 | 1/1985 | European Pat. Off. . |
| 0177915 | 4/1986 | European Pat. Off. . |
| 0267015 | 5/1988 | European Pat. Off. . |
| 9101152.3 | 7/1991 | Fed. Rep. of Germany . |
| 2432861 | 1/1974 | France . |
| WO83/04030 | 11/1983 | PCT Int'l Appl. . |
| WO85/00369 | 1/1985 | PCT Int'l Appl. . |

(List continued on next page.)

FOREIGN PATENT DOCUMENTS

| | | |
|---|---|---|
| WO86/02271 | 4/1986 | PCT Int'l Appl. . |
| 2092444A | 2/1982 | United Kingdom . |
| 2082213A | 3/1982 | United Kingdom . |
| 2092155 | 8/1982 | United Kingdom . |
| 2162851 | 7/1984 | United Kingdom . |

OTHER PUBLICATIONS

Brown et al., "Acceleration of Tensile Strength of Incisions Treated with EGF and TGF-beta", Ann. Surg., pp. 788 et seq. (Dec. 1988).

Barbul et al., eds., "Growth Factors and Other Aspects of Wound Healing/Biological and Clinical Implications", *Proceedings of the Second International Symposium on Tissue Repair*, Tarpon Springs, Florida, May 13–17, 1987 (Alan R. Liss, Inc., New York).

Biochemistry 1981, 20, 4667–4676.

Biochemistry 1981, 20, 4667–4686.

Lynch et al., "Growth Factors in Wound Healing" *J. Clin. Invest.*, vol. 84, Aug. 1989, 640–646.

Raychem RT-850 Product Specification RT-850 for Thermofit TM Kynar Tubing dated Mar. 6, 1984.

COMBINED SURGICAL NEEDLE-BRAIDED SUTURE DEVICE

CROSS REFERENCE TO RELATED APPLICATIONS

This application is a continuation-in-part of copending U.S. patent application Ser. No. 491,215, filed Mar. 9, 1990, now U.S. Pat. No. 5,019,093, as a continuation of then copending and now abandoned U.S. patent application Ser. No. 344,745, filed Apr. 18, 1989 as a continuation-in-part of then copending and now abandoned U.S. patent application Ser. No. 227,699, filed Aug. 3, 1988 as a continuation-in-part of then copending and now abandoned U.S. patent application Ser. No. 89,732, filed Aug. 26, 1987. This application is also a continuation-in-part of copending U.S. patent application Ser. No. 529,740, filed May 22, 1990, now U.S. Pat. No. 5,037,429, as a continuation of then pending and now abandoned U.S. patent application Ser. No. 89,735, filed Aug. 26, 1987, a continuation-in-part of U.S. patent application Ser. Nos. 221,308, filed Jul. 13, 1988, 395,476, filed Aug. 18, 1989 and 413,240, filed Sep. 27, 1989 and a continuation-in-part of copending U.S. patent application Ser. Nos. 89,733, filed Aug. 26, 1987 and 393,017, filed Aug. 10, 1989, all now abandoned the latter filed as a continuation of then copending and now abandoned U.S. patent application Ser. No. 89,734, filed Aug. 26, 1987. This application also relates by subject matter to concurrently filed U.S. patent application Ser. Nos. 07/570,345 filed Aug. 27, 1990, 07/569,063 filed Aug. 17, 1990 and 07/569,062 filed Aug. 17, 1990.

BACKGROUND OF THE INVENTION

The present invention relates to a combined surgical needle suture device and, more particularly, to such a device in which a shrinkable tubing attaches a braided suture of particular construction to a surgical needle.

For many years, surgeons have employed combined surgical needle-suture devices in which a suture, or ligature, is attached to the shank end of a surgical needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids and their cyclic dimers, glycolide and lactide.

Needle-suture combinations fall into two general classes: standard, or non-detachable, needle attachment and removable, or detachable, needle attachment. In the case of standard needle attachment, the suture is securely attached to the needle and is intended to be inseparable therefrom except by deliberate cutting or severing of the suture. Removable needle attachment, by contrast, is such that the needle is separable from the suture in response to a pulling or rupture force exerted by the surgeon. Minimum acceptable forces required to separate a needle from a suture (for various suture sizes) are set forth in the United States Pharmacopeia (USP). The USP prescribes minimum individual pull-out forces and minimum average pull-out forces as measured for five needle-suture combinations. The minimum pull-out forces for both standard and removable needle-suture attachment set forth in the USP are hereby incorporated by reference.

One typical method for securing a suture to a needle involves providing a cylindrical recess, or axial bore, in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. No. 2,928,395 (adhesives) and U.S. Pat. No. 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also known. For example, U.S. Pat. Nos. 3,980,975 and 3,980,177 teach swaging a suture within a needle bore such that the suture will have a pull-out value of from 3 to 26 ounces. Other detachable needle-suture attachment methods include providing a weakened suture segment (U.S. Pat. No. 3,949,756), tipping the end of a suture to be inserted in the axial bore of a needle with a lubricant (U.S. Pat. No. 3,963,031) and pretensioning a suture that is swaged within an axial needle bore (U.S. Pat. No. 3,875,946). See also, U.S. Pat. Nos. 3,799,169, 3,880,167, 3,924,630, 3,926,194, 3,943,933, 3,981,307, 4,124,027 and 4,127,133.

Another method for attaching a suture to a needle involves the use of a tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is further suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,110 relates to a flexible composite suture having a tandem linkage. The needle is secured to a flexible suture leader manufactured from a readily sterilizable plastic such as nylon, linear polyethylene, isotactic polypropylene, polyester, silk or other proteinaceous material, e.g., by inserting and crimping the suture leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 to Coplan describes a needle-suture attachment wherein a hollow suture portion is secured to the shank end of a needle which is of reduced cross-section compared with the remainder of the needle.

Additional patents which describe the use of a tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage lies in the possibility that foreign substances may inadvertently or uncontrollably be introduced into the needle bore, e.g., oil employed in the bore-drilling operation or silicone employed in a needle siliconization process. Measures taken to prevent or minimize the introduction of foreign materials into the needle bore, e.g., water blocking during the needle siliconization operation, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region. Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process and presents a tight, secure interface between needle (and/or suture) and tubing. The limited tolerance between the tubing inner diameter and the needle shank/suture outer diameters in such methods make these dimensions critical thereby making the attachment process more difficult and time-consuming and increasing the likelihood of attachment failure and/or rejected materials.

In addition to the foregoing deficiencies associated with known needle-suture attachment methods and the resulting needle-suture devices, the sutures themselves, when they are of multifilament construction, tend to exhibit disadvantages of their own. While currently available braided suture products are generally acceptable in terms of their knot-tying and knot-holding properties, as removed from the package, they tend to be stiff and wiry and retain a "set" or "memory" such that at the time of use, it is usually necessary for the surgeon or assistant personnel to flex and stretch the suture to make it more readily handible. Furthermore, the surfaces of known braided sutures are perceptibly rough. Thus, if one passes one's hand or fingers along the braid, surface irregularities will be readily detected. The result of this rough surface is that the suture will exhibit drag or chatter as it is drawn through tissue, characteristics which militate against smooth, neat, accurately placed wound approximation so necessary to excellence in surgical practice.

In the case of one braided suture now on the market, due to the necessity of having to meet fiber strength requirements while at the same time retaining acceptable knot-tying and knot-holding properties, the suture is constructed from a greater amount of fiber and consequently is of larger diameter than the accepted industry standard.

Accordingly, it is an object of the present invention to provide a surgical needle-braided suture attachment procedure which eliminates the need for drilling a bore in the needle shank and swaging the suture therein.

It is also an object of the invention to provide an attachment procedure which reliably secures the suture to the needle in an efficient manner without close tolerances between elements.

It is a further object to provide a surgical needle-suture attachment procedure which is flexible and atraumatic.

An additional object of the invention is to provide a combined surgical needle-braided suture device wherein separation of the needle from the suture is obtained by pulling the suture from the needle within a predetermined range of pull-out force.

Another particular object of this invention is to provide a combined surgical needle-braided suture device in which the braided suture component exhibits significantly reduced tissue drag compared with that of a comparably sized braided suture of known, or standard, construction.

SUMMARY OF THE INVENTION

By way of satisfying the foregoing objects as well as other objects of the invention, there is provided in accordance with this invention a method of attaching a surgical needle to a braided suture to provide a combined surgical needle-braided suture device which comprises:

a) providing a surgical needle possessing a shank end of reduced diameter;

b) providing a braided suture possessing a tip region for attachment to the shank end of the needle, the suture possessing a greater pick count and/or a greater number of sheath yarns for a suture of given overall denier than the pick count and/or number of sheath yarns of a standard braided suture of substantially the same overall denier;

c) placing a shrinkable tubing around the reduced diameter needle shank end and the tip region of the suture to be attached thereto; and, d) applying energy to the shrinkable tubing to bring the tubing into engagement with the shank end of the needle and the tip region of the suture thereby providing the combined surgical needle-braided suture device.

The combined surgical needle-braided suture device produced according to the present invention is atraumatic and advantageously exhibits flexibility in the attachment region. The physical and chemical characteristics of the shrinkable tubing material, the relative diameters of the tubing, the needle shank and the suture, and the amount of energy applied to the tubing may be controlled to provide a needle-suture combination having a desired pull-out force. It is thus possible to produce standard needle-braided suture combinations and removable needle-braided suture combinations using a single attachment process and a common inventory of materials.

As a result of its possessing a greater pick count and/or a greater number of sheath yarns for a suture of given overall denier and in some cases, a finer denier for the individual filaments making up a sheath yarn, the braided suture component of the combined surgical needle-suture device of this invention exhibits far fewer surface discontinuities thereby providing a suture which is considerably smoother and exhibits significantly reduced tissue drag than braided sutures of known construction.

In the description of the braided suture component of the combined surgical needle-braided suture device of this invention which follows, the term "suture" is intended to embrace both the non-absorbable as well as the bio-absorbable varieties, the term "braid" or "braided" refers to an arrangement of discrete units, or bundles, denominated "sheath yarns", made up of individual filaments with individual sheath yarns interlocking or interlacing each other in a regular criss-cross pattern and the term "pick count" refers to the number of crossovers of sheath yarns per linear inch of suture and, together with the overall denier of the suture, the denier of the individual filaments constituting a sheath yarn and the number of sheath yarns employed, defines the principal construction characteristics of the braided suture herein.

The term "standard suture" is intended to designate any of the heretofore known braided sutures, e.g., those described in U.S. Pat. No. 3,565,077, the contents of which are incorporated by reference herein, and in particular, braided suture products marketed by Ethicon, Inc. under its Vicryl brand and those marketed by Davis & Geck, Inc. (American Cyanamid Company) under its Dexon brand.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a method for effecting surgical needle-braided suture attachments and to such needle-braided suture combinations.

The invention has application to any suture material, whether absorbable or non-absorbable, natural or synthetic, and to any needle material and configuration, whether straight or curved.

Since the attachment method of this invention dispenses with the need for an axial bore drilling operation, it is now possible to employ particularly tough alloys which, although highly advantageous for use in the fabrication of surgical needles, have heretofore not been considered for this application due to the difficulty of machining a suture-receiving bore or socket therein. A particularly useful class of alloys for use in constructing the needle component of the needle-suture device of this invention are the quaternary alloys described in U.S. Pat. No. 3,767,385, the contents of which are incorporated by reference herein. These alloys contain from about 6 to about 25 weight percent iron and as principal alloying components therein, from about 18 to about 40 weight percent nickel, from about 6 to about 12 weight percent molybdenum from about 15 to about 25 weight percent chromium, the balance being cobalt. A preferred alloy of this type, Multiphase MP35N (SPS Technologies), contains 35 weight percent nickel, 35% cobalt, 20% chromium, 10% molybdenum with residual elements such as carbon, silicon, sulfur, and phosphorous being kept to as low a level as possible.

Figure 1:
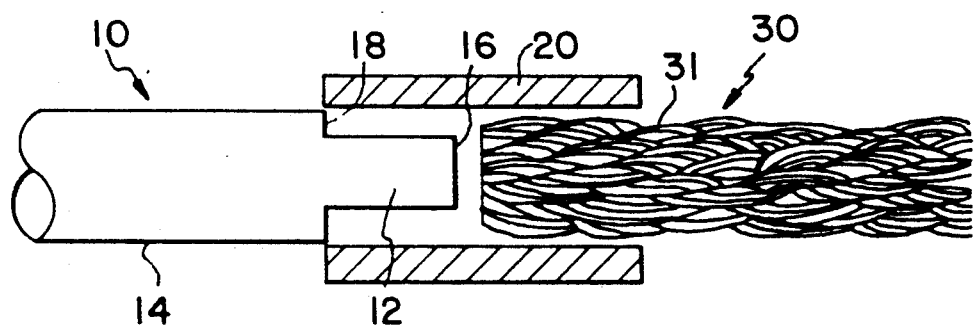
FIG. 1 is a side cross-sectional view of a needle and a braided suture with a shrinkable tubing positioned therearound (prior to engagement of the tubing with the needle and suture)
Figure 2:
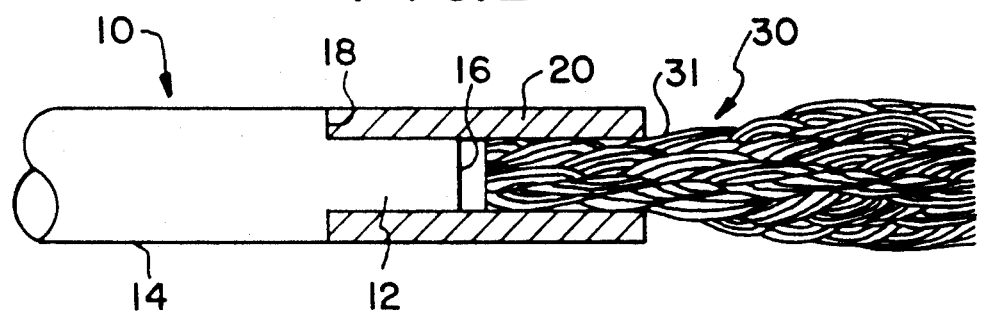
FIG. 2 is a side cross-sectional view of the tubing of FIG. 1 in engagement with the needle and the suture.
Figure 3:
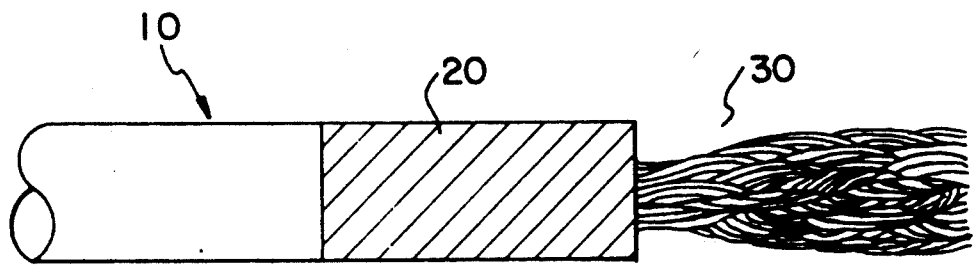
FIG. 3 is a side view of a combined surgical needle-braided suture device of the present invention.

Referring to FIGS. 1–3, surgical needle 10 possesses a reduced cross-sectional diameter at its shank end 12 relative to its remaining portion 14. The reduction in the diameter of shank end 12 can be achieved by any conventional means, e.g., by turning on a lathe. Typically, shank end 12 possesses a diameter which is from about 10 to about 65% smaller than the diameter of the remainder of needle 10, and preferably from about 25 to about 50% smaller. It is also possible to provide shank end 12 with a texturized surface to facilitate gripping by shrinkable tubing 20. For example, shank end 12 can be scored, ribbed or threaded, in whole or in part. It may also be desirable to taper shank end 12 such that distal end 16 of the shank will be of greater cross-sectional diameter than the cross-sectional diameter of shank end 12 where it meets shoulder 18, or vice versa.

Shank end 12 is placed within one end of shrinkable tubing 20 and braided suture 30 is positioned within the other end of the tubing as shown in FIG. 1. Shank end 12 of needle 10 and tip region 31 of suture 30 may abut or, as shown in FIGS. 1 and 2, there may be a gap between the two. As shown in FIG. 1, suture 30 may initially be of uniform cross-section throughout its length. Alternatively, tip region 31 of suture 30, i.e., the region inserted into tubing 20, may be of reduced cross-section relative to the remainder of suture 30, e.g., by tipping the suture tip region with an adhesive or resinous tipping agent while suture 30 is under tension. (See, e.g., Canadian Patent No. 1,009,532.) Resin tipping may be desirable to prevent brooming of the suture, particularly for multifilament braided sutures, thereby rigidifying tip region 31 of the suture to facilitate its handling during the attachment process. Tipping under tension can also allow a braided suture of larger diameter, e.g., a suture diameter equal to the diameter of the needle to which it is to be attached, to be more efficiently attached to the needle using shrinkable tubing 20. It is not necessary according to the present invention, however, to reduce the diameter of suture tip region 31 to efficiently attach needle 10 to suture 30. Indeed, it may be possible or desirable to apply a tipping agent to suture tip region 31 to prevent brooming without reducing its diameter. As shown in FIG. 1, shrinkable tubing 20 initially has an inner diameter that is larger than the outer diameter of suture tip region 31 thereby minimizing the importance of suture tipping.

After shrinkable tubing 20 is placed around shank end 12 of needle 10 and tip region 31 of suture 30, energy is applied to tubing 20. In response to this energy, tubing 20 contracts or shrinks and engages shank end 12 and tip region 31. The overall length of tubing 20 may also be affected by the application of energy, e.g., the length of tubing 20 may undergo reduction. Thus, the shrinking of tubing 20 brings the inner surface of tubing 20 into engagement with shank end 12 and suture tip region 31 thereby securing suture 30 to needle 10. Suitable energy sources include heat (convective or conductive), radiation, microwave energy, laser energy, etc.

As shown in FIGS. 1-2, shrinkable tubing 20 is simultaneously placed around both shank end 12 of needle 10 and tip region 31 of suture 30 in one embodiment of the present invention. It is preferable, however, to first secure shrinkable tubing 20 to shank end 12 of needle 10 and thereafter to suture tip region 31 of suture 30. Thus, in a preferred embodiment of the present invention, shrinkable tubing 20 is initially secured to shank end 12 through the localized application of energy to shrinkable tubing 20 in the region surrounding shank end 12. After tubing 20 has been brought into engagement with shank end 12, tip region 31 of suture 30 is inserted into tubing 20 and additional energy is applied thereto. Sequential shrinkage of tubing 20 makes it possible to vary the amount of energy used in securing tubing 20 to shank end 12 and suture tip region 31, respectively, and to limit the exposure of suture 30 to energy during the attachment process. It may also be desirable to cool suture 30 in the region outside tubing 20, e.g., by means of a curtain of cold air or other gaseous coolant, to prevent or minimize any degradation of the suture. As shown in FIGS. 2 and 3, the shrinkage of tubing 20 typically compresses suture tip region 31 to some extent, e.g., from 30 to 35% or so.

Shrinkable tubing 20 can be manufactured from any material which shrinks, i.e., reduces in diameter, in response to the application of energy. Suitable materials include "memory metals", e.g., nickel-titanium mixtures, nickel-iron-titanium mixtures, or copper based materials, as are well known in the art (see, e.g., U.S. Pat. Nos. 3,759,552, 3,801,954, 4,198,081, and 4,773,680) and shrinkable plastic materials such as polyolefins. Shrinkable polyvinylidene fluoride materials available from Raychem Corporation, Menlo Park, Calif. under the tradename Kynar have been used with generally good results. Where shrinkable plastic materials are employed, the tubing is typically extruded so that its inner diameter will be less than the final desired inner diameter, i.e., the inner diameter of the tubing following application of energy which results in shrinkage of the tubing. Following extrusion, the tubing is expanded radially outward through radial expansion means to provide a tubing of expanded inner diameter as shown, for example, by tubing 20 in FIG. 1. Such plastic tubing is thus adapted to shrink, or "recover", to its original extruded inner diameter in response to the application of a predetermined amount of energy.

The amount of energy applied to shrinkable tubing 20 to effect the desired attachment, i.e., diameter reduction, depends upon the chemical characteristics of the tubing material, the relative dimensions of the tubing, the shank end of the needle and the suture, and the desired pull-out force for the resulting combined surgical needle-braided suture device. For example, one polyvinylidene fluoride material available from Raychem Corporation (RT-850) shrinks at temperatures greater than 175° C. and is adapted to recover to about 50% of its radially expanded inner diameter. In such case, tubing 20 may be brought into engagement with shank end 12 of needle 10 and suture tip region 31, either simultaneously or sequentially, by heating tubing 20 to a temperature above 175° C. Tubing 20 may be heated through contact with a hot gas stream or with heated dies, or by other heating means. Typically, the outer diameters of shank end 12 and suture tip region 31 are greater than the fully recovered diameter of tubing 20, e.g., greater than 50% of the initial inner diameter of tubing 20 for the RT-850 material, such that tubing 20 engages shank end 12 and suture tip region 31. This engagement provides the combined surgical needle-braided suture device of the present invention.

As noted above, the attachment method of the present invention may be easily used to effect both standard needle attachment and detachable needle attachment. Preferably, the pull-out force of a given needle-braided suture combination is controlled through control of the energy source. Thus, using the identical inventories of needles, braided sutures and tubings, it is possible to produce either standard or detachable combined surgical needle-braided suture devices through simple energy variations. In the case of detachable needle attachment, it is preferred that the attachment conditions be controlled such that the tubing remains secured to the needle once the suture is detached.

The needle-braided suture attachment method of the present invention has many advantages over previous attachment methods. Machining of the needle to provide a reduced diameter needle shank is much easier and more controllable than bore drilling operations and therefore permits the use of needle alloys which have previously been impractical, e.g., Series 300 stainless steel and quaternary alloys such as those disclosed in U.S. Pat. No. 3,767,385 referred to above. These heretofore impractical alloys have advantageous strength and ductility characteristics as compared to conventionally used Series 400 stainless steels. Moreover, an unreliable, expensive and maintenance-intensive swaging process is replaced by a sterile, controllable and relatively inexpensive energy supply. The tubing used in the present invention may be color coded to designate suture material, standard versus detachable attachment, etc., particularly where a plastic tubing is employed.

The attachment method of the present invention is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may be recovered and reused thereby greatly reducing processing waste. The range of acceptable suture diameters is greatly expanded due to the ability of the tubing to recover or shrink to varying degrees, thereby minimizing the likelihood that suture production will be rejected for inability to attach needles thereto. A single tubing size may be used to attach several needle sizes because the shrinkable tubing is capable of recovering or shrinking to varying degrees. This greatly simplifies inventory considerations.

In a preferred embodiment, braided suture component 30 is fabricated from a bio-absorbable or biodegradable resin such as one derived from polyglycolic acid, glycolide, lactic acid, lactide, dioxanone, trimethylene carbonate, etc., and various combinations of these and related monomers. Sutures prepared from resins of this type are known in the art, e.g., as disclosed in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459–1464 (1979), and D. F. Williams (ed.), *Biocompatibility of Clinical Implant Materials*, Vol. II, ch. 9: "Biodegradable Polymers" (1981).

The defining characteristics of the braided suture of this invention, apart from the material of its construction, are:

(1) overall suture denier;
(2) the pattern of the interlocking yarns expressed as the pick count, which is to say, the number of crossovers of individual sheath yarns per linear inch of suture;
(3) the number of sheath yarns comprising the braid;
(4) the denier of the individual filaments comprising each sheath yarn; and,
(5) the denier of the core, where present.

(1) Overall Denier of the Suture

The overall denier of braided suture 30 can vary from about 50 to about 4000. Within this range, the ranges of overall denier for particular sutures are: from about 50 to about 125 denier; from above about 125 to about 200 denier; from above about 200 to about 300 denier; from above about 300 to about 500 denier; from above about 500 to about 800 denier; from above about 800 to about 1500 denier; from above about 1500 to about 2000 denier; and, from above about 2000 to about 3600 denier.

(2) Pattern of the Interlocking Sheath Yarns (Pick Count)

For a braided suture 30 of any range of overall denier, pick count can vary from about 50 to about 100 crossovers/inch with about 55–80 crossovers/inch being preferred. For sutures constructed within any range of overall denier, as larger numbers of sheath yarns are employed, the pick-count for acceptable sutures will also increase within the above ranges.

For a suture of a particular range of denier and number of sheath yarns, pick count is advantageously established to achieve a balance in the properties desired. In general, with increasing pick count, surface roughness of the suture tends to increase and with decreasing pick count, the ability of the external braided sheath to contain the core (if present) tends to decrease even reaching the point where the braid may become so loose as to result in the core protruding therethrough.

For sutures of any specific denier range and number of sheath yarns, it is preferable to have as low a pick count as possible in order to achieve optimum surface smoothness, consistent, of course, with the need to provide a compact braid which prevents the core (if present) from protruding through the exterior sheath yarn structure.

(3) The Number of Sheath Yarns

The number of sheath yarns bears some relation to overall suture denier, the number generally increasing with the weight of suture component 30. Thus, across the range of suture weight (denier) indicated above, the braided suture of this invention can be constructed with from about 4 up to as many as about 36 individual sheath yarns constructed from individual filaments having the deniers discussed below.

Table I below sets forth broad and preferred ranges for the numbers of sheath yarns which are suitable for the construction of braided sutures of various ranges of overall denier. The pick counts of the sutures vary from about 50 to about 100 and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 1.0 to about 1.8, for the preferred range of number of sheath yearns.

TABLE I

| Sheath Yarns Related to Suture Denier | | | |
|---|---|---|---|
| Overall Suture Denier | Suture Size | Number of Sheath Yarns (Broad Range) | Number of Sheath Yarns (Preferred Range) |
| 50 to about 125 | 7/0, 8/0 | 4–16 | 6–14 |
| greater than about 125 to about 200 | 6/0 | 4–16 | 6–14 |
| greater than about 200 to about 300 | 5/0 | 4–16 | 6–14 |
| greater than about 300 to about 500 | 4/0 | 10–20 | 12–14 |
| greater than about 500 to about 800 | 3/0 | 14–20 | 14–18 |
| greater than about 800 to about 1200 | 2/0 | 16–32 | 20–30 |
| greater than about 1200 to about 2000 | 0 | 20–36 | 24–34 |
| greater than about 2000 to about 4000 | 1, 2 | 20–36 | 24–34 |

While the sheath yarns need not be twisted, it is generally preferred that they be provided with a twist so as to minimize snagging during braid construction.

(4) Individual Filament Denier

The individual filaments comprising each sheath yarn can vary in weight from about 0.2 to about 6.0 denier, preferably from about 0.8 to about 3.0 denier and more preferably from about 1.0 to about 1.8 denier. The number of such filaments present in a particular sheath yarn will depend on the overall denier of the suture as well as the number of sheath yarns utilized in the construction of the suture. Table II sets forth some typical numbers of filaments per sheath yarn for both the broad and preferred ranges of filament weight:

TABLE II

| Number of Filaments per Sheath Yarn | | |
|---|---|---|
| approximate minimum | approximate maximum | Filament Denier |
| 45 | 50 | 0.2 |
| 15 | 150 | 0.5 |
| 5 | 50 | 1.5 |
| 3 | 40 | 1.8 |
| 1 | 15 | 6.0 |

(5) Core (Optional)

For all but the lowest range of overall denier, braided suture 30 can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier denier to possess a core. Where a core is provided, it is generally preferred that it possess a weight which is significantly greater than that of a core of a known suture of equivalent overall denier.

Table III below provides some typical core deniers for sutures of various deniers.

TABLE III

| Core Denier Related to Suture Denier | | | |
|---|---|---|---|
| Overall Suture Denier | Suture Size | Denier of Optional Core (Broad Range) | Denier of Optional Core (Preferred Range) |
| from about 50 to about 125 | 8/0, 7/0 | none | none |
| greater than about 125 to about 200 | 6/0 | 20–80 | 25–50 |
| greater than about 200 to about 300 | 5/0 | 30–100 | 50–80 |
| greater than about 300 to about 500 | 4/0 | 80–50 | 80–120 |
| greater than about 500 to about 800 | 3/0 | 150–300 | 180–280 |
| greater than about 800 to about 1200 | 2/0 | 250–700 | 350–650 |
| greater than about 1200 to about 2000 | 0 | 400–1200 | 500–1000 |
| greater than about 2000 to about 4000 | 1, 2 | 800–2400 | 1000–2200 |

When braided suture component 30 is fabricated from a material which is susceptible to hydrolysis, e.g., any of the absorbable resins previously mentioned, care must be take to rigorously exclude moisture from contacting the suture during storage or to otherwise preserve the suture from excessive hydrolytic attack which would compromise its in vivo strength to the point where the suture would no longer be serviceable.

According to U.S. Pat. Nos. 3,728,839 and 4,135,622, the in vivo strength of polyglycolic acid surgical elements such as sutures undergoes significant deterioration on long term storage in the package even on exposure of the contents to very small amounts of water for very short periods of time, e.g., 20 minutes or less, just prior to packaging due to the tendency of a moisture impervious package to seal the moisture in with the suture. To prevent or minimize excessive hydrolytic degradation of an absorbable suture during storage, U.S. Pat. Nos. 3,728,839 and 4,135,622 disclose removing moisture from the suture before sealing the package so that no more than about 0.5 percent of water by weight of suture remains in the package once the package is sealed. This approach to improving the suture's storage stability, while effective, is in practice difficult and expensive to carry out. Prior to sealing the suture within its moisture impervious package, it is essential that the suture be "bone dry", a condition achieved by heating the suture for a sufficient period to remove the water therefrom, e.g., 180°–188° for 1 hour under a 26 inch vacuum. However, once the water is removed, the suture cannot be allowed to contact a moisture-containing environment even for a limited duration since as previously noted, even brief exposure to moisture can cause severe deterioration of suture in vivo strength. It therefore becomes necessary following the water removal step to temporarily store the suture in a dry area, i.e., an environment which is essentially free of moisture, where the possibility of contact with moisture is largely eliminated. These operations for improving the storage stability of an absorbable suture are time consuming, expensive and constitute a relatively complex solution to the storage stability problem.

In an entirely different approach to improving the storage stability of an absorbable suture, one that avoids the foregoing drawbacks associated with the method of U.S. Pat. Nos. 3,728,839 and 4,135,622, the storage stability of an absorbable braided suture which is susceptible to hydrolysis is improved by applying to the suture a storage stabilizing amount of at least one water soluble liquid polyhydroxy compound and/or ester thereof as disclosed in commonly assigned, copending U.S. patent application Ser. No. 89,735, filed Aug. 26, 1987, the contents of which are incorporated by reference herein. In addition to imparting an enhanced degree of storage stability to the suture, practice of this embodiment of the present invention confers other benefits as well. So, for example, a braided suture which has been filled with a storage stabilizing amount of, e.g., glycerol, exhibits better flexibility and "hand" characteristics than the untreated suture. Moreover, since the polyhydroxy compounds are generally capable of dissolving a variety of medico-surgically useful substances, they can be used as vehicles to deliver such substances to a wound or surgical site at the time the suture is introduced into the body.

The useful storage stabilizing agents are generally selected from the water soluble liquid polyhydroxy compounds and/or esters of such compounds, preferably those having no appreciable toxicity for the body at the levels present The expression "liquid polyhydroxy compound" contemplates those polyhydroxy compounds which in the essentially pure state are liquids, as opposed to solids, at or about ambient temperature, e.g., at from about 15° C. to about 40° C. The preferred polyhydroxy compounds possess up to about 12 carbon atoms and where the esters are concerned, are preferably the monoesters and diesters.

Among the specific storage stabilizing agents which can be used with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of storage stabilizing agents, e.g., sorbitol dissolved in glycerol, glycerol combined with monoacetin and/or diacetin, etc., are also useful.

To prevent or minimize run-off or separation of the storage stabilizing agent from the suture, a tendency to which relatively low viscosity compounds such as glycerol are somewhat prone, it can be advantageous to combine the agent with a thickener. Many kinds of pharmaceutically acceptable non-aqueous thickeners can be utilized including water-soluble polysaccharides, e.g., hydroxypropyl methylcellulose (HPMC), and the other materials of this type which are disclosed in European Patent Application 0 267 015 referred to above, polysaccharide gums such as guar, xanthan, and the like, gelatin, collagen, etc. An especially preferred class of thickeners are the saturated aliphatic hydroxycarboxylic acids of up to 6 carbon atoms and the alkali metal and alkaline earth metal salts and hydrates thereof. Within this preferred class of compounds are those of the general formula

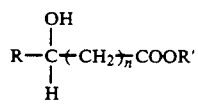

wherein R is hydrogen or a methyl group, R' is hydrogen or a metal selected from the group consisting of alkali metal and alkaline earth metal and n is 0 or 1 and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as the calcium, potassium and sodium salts thereof, and the like. As stated hereinbefore, hydrates of these compounds can also be used. Calcium lactate, especially calcium lactate pentahydrate, is a particularly preferred thickener.

Where a thickener is utilized, it will be incorporated in the filling composition in at least that amount required to increase the overall viscosity of the composition to the point where the composition no longer readily drains away from the suture in a relatively short period. In the case of a preferred storage stabilizing agent-thickener combination, namely, glycerol and calcium lactate, the weight ratio of glycerol to calcium lactate can vary from about 1:1 to about 10:1 and preferably is from about 6:1 to about 8:1.

If necessary or desirable, the storage stabilizing agent together with optional thickener can be dissolved in any suitable non-aqueous solvent or combination of solvents prior to use. To be suitable, the solvent must (1) be miscible with the storage stabilizing agent and optional thickener, (2) have a sufficiently high vapor pressure to be readily removed by evaporation, (3) not appreciably affect the integrity of the suture and (4) be capable of wetting the surface of the suture. Applying these criteria to a preferred storage stabilizing agent, glycerol, advantageously in admixture with a preferred thickener, calcium lactate, lower alcohols such as methanol and ethanol are entirely suitable solvent carriers. When a solvent is utilized in the preparation of the stabilizing agent, such solvents, e.g., methanol, can be employed in amounts providing a solution concentration of from about 20% to about 50%, preferably about 30% to about 45%, by weight of the storage stabilizing agent including any optional thickener based on the total weight of the solution.

Preparing the storage stabilizing agent for application to the suture is a relatively simple procedure. For example, in the case of a mixture of glycerol and calcium lactate, the desired amount of glycerol is first introduced to a suitable vessel followed by the addition thereto of the desired amount of calcium lactate. If no solvent is to be used, the mixture is then thoroughly mixed. Where a solvent such as methanol is employed, the solvent is added to the mixture of glycerol and calcium lactate and the solution is then thoroughly mixed to dissolve the compounds.

Application of the storage stabilizing agent to the suture can be carried out in any number of ways. Thus, for example, the suture can be submerged in the storage stabilizing agent or solution thereof until at least a storage stabilizing amount of agent is acquired or otherwise retained by the suture, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the treated suture compared to the same suture which has not been treated with storage stabilizing agent. It has been found that calendaring the suture prior to filling, such as by passing the suture through at least two pairs of transversely mounted calendar rolls, improves receptivity of the suture to filling and improves the suppleness of the resulting filled suture. It is believed that calendaring the suture separates the individual suture filaments to open up spaces therebetween which are conducive to ensuring that the filling composition penetrates within, and fills, the interstices of the braided suture.

The foregoing submersion method of contacting the suture with storage stabilizing agent can be conducted continuously or in batch. Thus, a running length of the suture can be continuously passed through a quantity of the stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. Preferably, the suture is passed through a coating head supplied by a metering pump with a constant supply of filling solution, with the suture emerging from the coating head and passing through an evaporation oven to remove the filling solution solvent prior to any further surface contact, i.e., with rollers, etc. In a batch operation, a quantity of suture is merely submerged within the storage stabilizing agent for the requisite period of time with any excess agent being removed from the suture if desired.

Alternatively, the storage stabilizing agent and solutions thereof can be applied to the suture by spraying, brushing, wiping, etc., such that the suture receives and retains at least a storage stabilizing amount of the agent. Yet another procedure which can be used to apply the storage stabilizing agent involves inserting the suture in a package containing an effective amount of the agent such that intimate contact between the suture and the agent is achieved.

Whatever the contacting procedure employed, it is necessary that the suture being treated acquire a storage stabilizing amount of the storage stabilizing agent. In general, amounts of from about 2 to about 25, and preferably from about 5 to about 15 weight percent, of storage stabilizing agent(s) (exclusive of any solvent) by weight of the suture contacted therewith is sufficient to provide significantly improved storage stability compared to that of the untreated suture.

As previously pointed out, a filled braided suture component in accordance with the invention need not be packaged and maintained under the very dry conditions required for prior synthetic absorbable sutures. Instead, it is preferred that the filled sutures be equilibrated so that the level of moisture or other stabilizing agent solvent is sufficient to result in an appropriate viscosity level for the stabilizing agent and thickener in order to keep the stabilizing agent on the suture. In the preferred embodiment of a braided suture filled with a mixture of glycerol and calcium lactate, the moisture level may be equilibrated to as low as about 0.2% by weight of the suture, and is preferably above 0.3% or, even more preferably, about 0.5% by weight of the suture.

Indeed, it has been found that a braided suture filled with a glycerol/calcium lactate composition tends to undergo undesirable changes if exposed to a very dry environment. More particularly, if such a filled suture is exposed to a very dry environment, the surface of the suture may accumulate a flaked or powdered substance which could possibly interfere with, or render more difficult, the removal of the suture from its package. Equilibrating the filled suture, such as in a dew point controlled environment, so that the suture contains a relatively high moisture level, e.g., in excess of 0.2% and preferably in excess of 0.5% by weight of the suture, prevents such accumulation of flaked or powdered substance which might otherwise result were the suture exposed to an extremely dry environment. Conversely, the presence of too much moisture can also have deleterious effects, such as causing the glycerol filling to run. Therefore, it is preferable to control the moisture level within a range having preset upper and lower limits.

It is also within the scope of this invention to impregnate the braided suture with, or otherwise apply thereto, one or more medico-surgically useful substances, e.g., those which accelerate or beneficially modify the healing process when the suture is applied to a wound or surgical site. So, for example, the suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the spiroid braided suture of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and includes their biologically active closely related derivatives. The HGFs can be derived from naturally occurring sources including human and non-human sources, e.g., bovine sources, and are preferably produced by recombinant DNA techniques. Specifically, any of the HGFs which are mitogenically active and as such are effective in stimulating, accelerating, potentiating or otherwise enhancing the wound healing process can be usefully applied to the suture herein, e.g., hEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497, 3,917,824, 3,948,875, 4,338,397, 4,418,691, 4,528,186, 4,621,052, 4,743,679 and 4,717,717, 4,861,757, 4,874,746 and 4,944,948, European Patent Application Nos. 046,039, 128,733, 131,868, 136,490, 147,178, 150,572, 177,915 and 267,015, PCT International Applications WO 83/04030, WO 85/003698, WO 85/01284 and WO 86/02271 and UK Patent Applications GB 2 092 155 A, 2 162 851 A and GB 2 172 890 A and, "Growth Factors in Wound Healing", Lynch, et al., *J. Clin. Invest.*, Vol. 84, pages 640–646 (August 1989), all of which are incorporated by reference herein. Of the known HGFs, hEGF, TGF-beta, IGF, PDGF and FGF are preferred, either singly or in combination.

In a preferred embodiment of the combined surgical needle-braided suture device of this invention, a filling composition comprising a surgical wound healing enhancing amount of at least one HGF and as carrier therefor at least one water soluble, liquid polyhydroxy compound and/or ester thereof such as any of those previously mentioned is applied to the suture component. The carrier protects the HGF component of the filling composition from excessive degradation or loss of biopotency during storage and as disclosed above, when the suture is fabricated from an absorbable resin which is susceptible to hydrolysis, the carrier improves the storage stability of the suture as well. In addition to carrier, the HGF can contain a thickener such as any of those previously mentioned in order to reduce or limit the tendency of carrier run-off.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See, e.g., Tomlinson (Ciba-Geigy Pharmaceuticals, West Sussex, U.K.), "Selective Delivery and Targeting of Therapeutic Proteins", a paper presented at a symposium held Jun. 12–14, 1989 in Boston, Mass., the contents of which are incorporated by reference herein. The HGFs can also be associated with carrier proteins (CPs), e.g., in the form of CP-bound HGF(s), to further enhance availability of the HGF(s) at a wound site as disclosed in "Carrier Protein-Based Delivery of Protein Pharmaceuticals", a paper of Bio- Growth, Inc., Richmond, Calif. presented at the aforementioned symposium, the contents of said paper being incorporated by reference herein. The HGFs can also be incorporated in liposomes to provide for their release over an extended period. Lactate ion can be present to augment the wound healing activity of the HGF. Protectants for the HGF can also be utilized, e.g., polyethylene glycols, acetoxyphenoxy polyethoxy ethanols, polyoxyethylene sorbitans, dextrans, albumin, poly-D-alanyl peptides and N-(2-hydroxypropyl)-methacrylamide (HPMA).

The amounts of HGF, carrier and optional component(s) such as thickener, site-specific hybrid protein, carrier protein, etc., identified above can vary widely and in general will be at least that amount of a particular component which is required to perform its respective function in an effective way. Those skilled in the art employing known or conventional procedures can readily determine optimum amounts of each component for a particular filling composition and particular braided suture filled therewith.

In general, the HGF(s) can be present in the total composition at a level ranging from about 0.1 to about 25,000 micrograms per gram of such composition, preferably from about 0.5 to about 10000 micrograms per gram of composition and most preferably from about 1 to about 500 micrograms per gram of composition.

Application of the HGF-containing composition to braided suture component 30 can be carried out by any suitable technique, e.g., by any of the procedures described above for applying a storage stabilizing agent to the suture.

It can also be advantageous to apply one or more coating compositions to braided suture component 30 where particular functional properties are desired. For example, the suture can be coated with a material which improves its surface lubricity and/or knot tie-down characteristics. Suitable materials which impart either or both characteristics include the bioabsorbable coating compositions obtained by copolymerizing in accordance with known procedures (1) a polyether glycol selected from the group consisting of relatively low molecular weight polyalkylene glycol, e.g., one corresponding to the general formula $HO(RO)_yH$ wherein R is an alkylene group of from 2–4 carbon atoms and y is an integer of from about 100–350, and polyethylene oxide-polypropylene oxide block copolymer, e.g., one corresponding to the general formula $H(OCH_2CH_2)_x$-$(OC_3H_6)_y(OCH_2CH_2)_zOH$ wherein x is an integer of from about 45–90, y is an integer of from about 60–85 and z is an integer of from about 45–90 with (2) a mixture of lactide monomer and glycolide monomer or a preformed copolymer of lactide and glycolide, the weight ratio of (1) to (2) preferably ranging from 4:1 to about 1:4 and more preferably from about 2:1 to about 1:2. The ratio of lactide to glycolide in the monomer mixture or in the copolymer of these monomers preferably varies from about 65–90 mole percent lactide and 10–35 mole percent glycolide. Polyether glycols which can be used to prepare the bioabsorbable coating compositions advantageously include polyethylene glycols having molecular weights of about 3,500–25,000 and preferably from about 4,000–10,000 and polyethylene oxide-polypropylene oxide block copolymers having molecular weights of from about 5,000–10,000 and preferably from about 7,500 to about 9,000, e.g., those disclosed in U.S. Pat. Nos. 2,674,619, 3,036,118, 4,043,344 and 4,047,533 and commercially available as the Pluronics (BASF-Wyandotte). Where preformed copolymers of lactide and glycolide are employed in preparing the bioabsorbable coating compositions, they may be prepared as described in U.S. Pat. No. 4,523,591. The amounts of bioabsorbable coating composition to be applied to the suture, e.g., by coating, dipping, spraying or other appropriate technique, will vary depending upon the specific construction of the suture, its size and the material of its construction. In general, the coating composition applied to an unfilled suture will constitute from about 1.0 to about 3.0 percent by weight of the coated suture, but the amount of coating add-on may range from as little as about 0.5 percent, by weight, to as much as 4.0 percent or higher. For a preferred filled (i.e. containing a storage stabilizing agent) braided suture, amounts of coating composition will generally vary from about 0.5% to 2.0% with as little as 0.2% to as much as 3.0%. As a practical matter and for reasons of economy and general performance, it is generally preferred to apply the minimum amount of coating composition consistent with good surface lubricity and/or knot tie-down characteristics. This level of coating add on is readily determined experimentally for any particular suture.

The following examples are illustrative of various embodiments of braided suture component 30 of the combined surgical needle- braided suture device of this invention.

COMPARISON EXAMPLES 1–7

The following braided suture configurations are disclosed in U.S. Pat. No. 3,565,077:

| Comparison Example | Overall Suture Denier | Pick Count | Number of Sheath Yarns | Denier of Individual Filaments | Denier of Core |
|---|---|---|---|---|---|
| 1 | 175 | 40 | 6 | 6 | 25 |
| 2 | 300 | 46 | 8 | 6 | 100 |
| 3 | 500 | 40 | 8 | 6 | 100 |
| 4 | 800 | 50 | 12 | 6 | 200 |
| 5 | 1200 | 50 | 16 | 6 | 400 |
| 6 | 1500 | 50 | 12 | 6 | 600 |
| 7 | 2000 | 40 | 16 | 6 | 800 |

Sutures possessing approximately these configurations are relatively inflexible, rough-surfaced and exhibit a relatively high level of chatter and drag.

COMPARISON EXAMPLES 8–11

The following braided suture configurations are those of four commercially available sutures:

| Example | Overall Suture Denier | Suture Size | Pick Count | Number of Sheath Yarns | Denier of Individual Filaments | Denier of Core |
|---|---|---|---|---|---|---|
| 8 | 259 | 5/0 | 47 | 8 | 2.1 | 29 |
| 9 | 698 | 3/0 | 52 | 12 | 2.1 | 55 |
| 10 | 1566 | 0 | 50 | 16 | 2.1 | 252 |
| 11 | 2122 | 1 | 44 | 16 | 2.2 | 330 |

Photomicrographs obtained by scanning electron microscopy (SEM) of the suture of Comparison Example 10 (FIGS. 4 and 5: cross-sectional view at 200x and linear view at 50x, respectively) clearly show the structural details of the suture. The suture braid is made up of relatively few sheath yarns and the circumferential indentations, plainly evident in FIG. 4, cause the braid surface to be relatively rough.

EXAMPLES 1-8

These examples illustrate various sizes of braided suture 30 constructed in accordance with the present invention.

| Comparison Example | Overall Suture Denier | Suture Size | Pick Count | Number of Sheath Yarns | Denier of Individual Filaments | Denier of Core |
|---|---|---|---|---|---|---|
| 1 | 96 | 7/0 | 82 | 8 | 1.2 | — |
| 2 | 173 | 6/0 | 75 | 12 | 1.2 | 29 |
| 3 | 240 | 5/0 | 65 | 8 | 1.2 | 48 |
| 4 | 389 | 4/0 | 75 | 12 | 1.2 | 101 |
| 5 | 600 | 3/0 | 65 | 16 | 1.2 | 216 |
| 6 | 1080 | 2/0 | 72 | 24 | 1.2 | 504 |
| 7 | 1378 | 0 | 65 | 28 | 1.2 | 706 |
| 8 | 2028 | 1 | 65 | 32 | 1.2 | 1260 |

Comparing the details of construction of the foregoing braided sutures with those of the known braided sutures as set forth in Comparison Examples 1-11, it will be noted that for sutures of comparable overall denier, the suture of this invention possesses a significantly greater pick count and number of sheath yarns and a significantly finer denier for the individual filaments making up a sheath yarn than the equivalent characteristics of the known suture.

As a result of their unique construction characteristics, suture component 30 of this invention exhibits perceptibly improved flexibility and hand and reduced chatter and drag compared with the known, or standard, sutures of Comparison Examples 1-11. For a given suture size, a braided suture component of the combined surgical needle-braided suture device of this invention will typically exhibit a level of tissue drag not exceeding about 60%, preferably not exceeding about 40% and more preferably, not exceeding about 20%, of the tissue drag of a standard braided suture of comparable size.

EXAMPLES 9-12

The following braided sutures were fabricated in accordance with the present invention:

| Example | Overall Suture Denier | Suture Size | Pick Count | Number of Sheath Yarns | Denier of Individual Filaments | Denier of Core |
|---|---|---|---|---|---|---|
| 9 | 240 | 5/0 | 68 | 8 | 1.2 | 40 |
| 10 | 600 | 3/0 | 71 | 16 | 1.2 | 180 |
| 11 | 1374 | 0 | 67 | 28 | 1.2 | 702 |
| 12 | 2230 | 1 | 57 | 32 | 1.2 | 975 |

In contrast to the suture of Comparison Example 10, supra, SEM photomicrographs of the suture of Example 11 (FIGS. 6 and 7: cross-sectional view at 200x and linear view at 50x, respectively) show a smooth circumferential surface as the result of the increased number of sheath yarns and smaller diameter of individual filaments.

Figure 4:
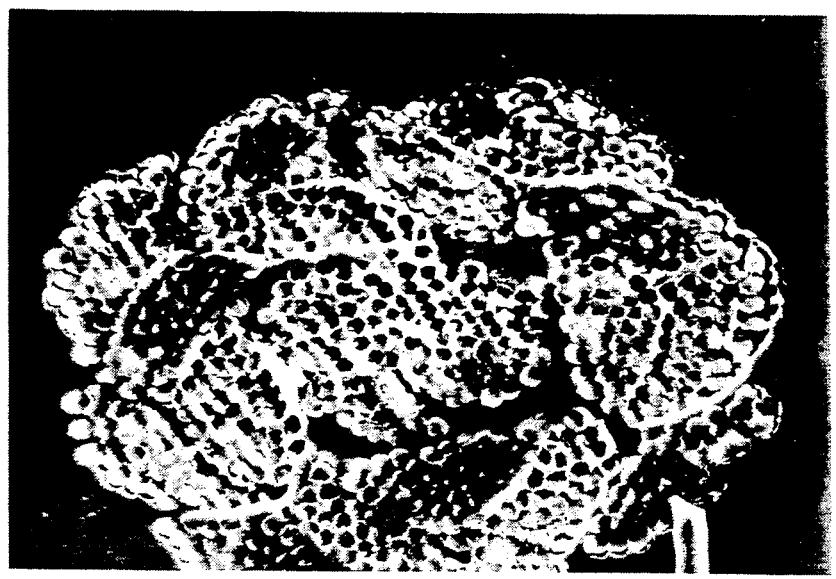
FIGS. 4–13 are photomicrographs of cross-sectional and linear views of braided sutures both within (FIGS. 6, 7 and 10 to 13) and outside (FIGS. 4, 5, 8 and 9) the scope of this invention, the latter being presented for comparison purposes; and, FIG. 14 is a graphical representation of the tissue drag performance of the braided suture component of a combined surgical needle-braided suture device of this invention compared with that of two known types of braided sutures of equivalent size.
Figure 6:
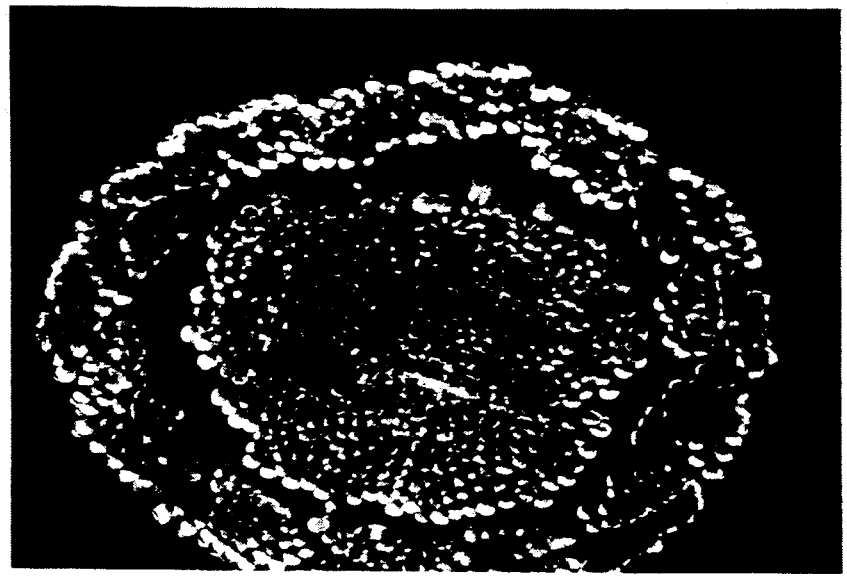

FIG. 4 as compared to FIG. 6 shows the relatively larger core present in the suture of Example 11 as compared to that of Comparison Example 10.

Figure 5:
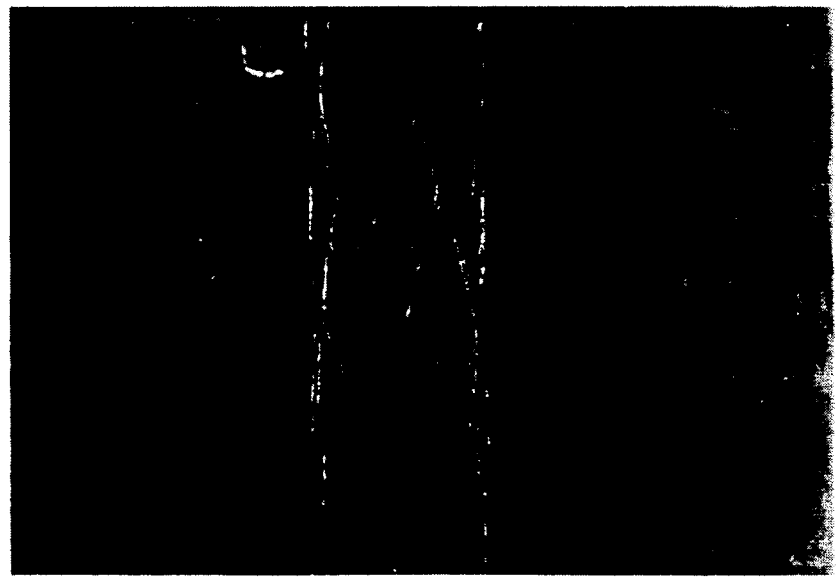
Figure 7:
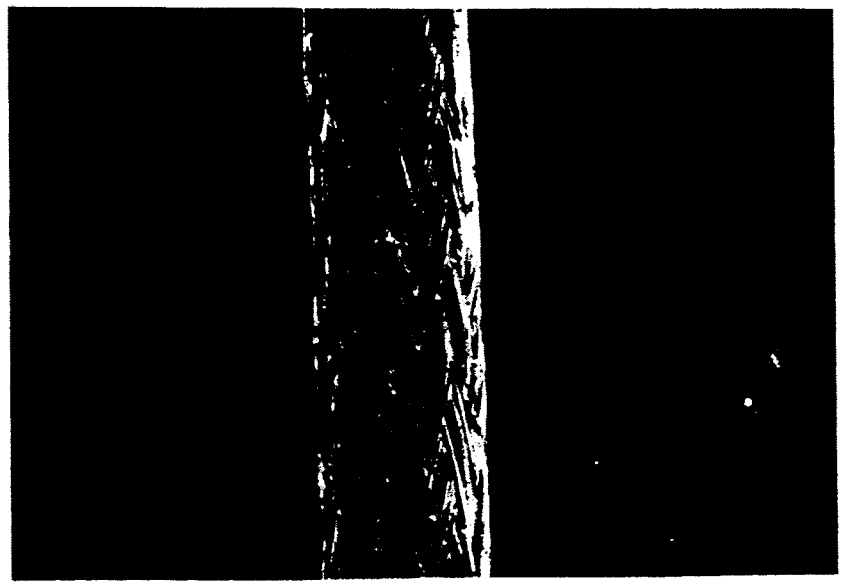

Comparison between FIGS. 5 and 7 shows the increased number of picks (crossovers/inch) of the suture of Example 11 as compared to that of Comparison Example 10.

EXAMPLES 13-15

The following suture braids were fabricated in accordance with the present invention:

| Example | Overall Suture Denier | Suture Size | Pick Count | Number of Sheath Yarns | Denier of Individual Filaments | Denier of Core |
|---|---|---|---|---|---|---|
| 13 | 1442 | 0 | 70 | 28 | 2.0[1] | 882 |
| 14 | 1621 | 0 | 70 | 28 | 1.2 | 882 |
| 15 | 1554 | 0 | 78 | 28 | 1.2 | 882 |

[1]Denier of sheath filaments; core filaments were 1.2 dpf.

The suture braids were coated to improve suture lubricity and knot tie-down characteristics and compared for physical properties for diameter USP knot-pull and suture tissue drag with the coated commercial suture of Comparison Example 10.

In this tissue drag test, sutures were needled with identical tapered needles to normalize any effect of needle diameter on the test.

Sutures were passed through live animal abdominal fascia tissue. The results of the tissue drag study are shown in Table IV as follows:

TABLE IV

| | Tissue Drag Results | | |
|---|---|---|---|
| Example | Diameter (min) | Knot-Pull (Kg) | Tissue Drag (gms force, maximum) |
| Comparison Example 10 | 0.419 | 4.72 | 257 |
| 13 | 0.413 | 5.27 | 35 |
| 14 | 0.428 | 5.35 | 56 |
| 15 | 0.444 | 5.04 | 50 |

Figure 8:
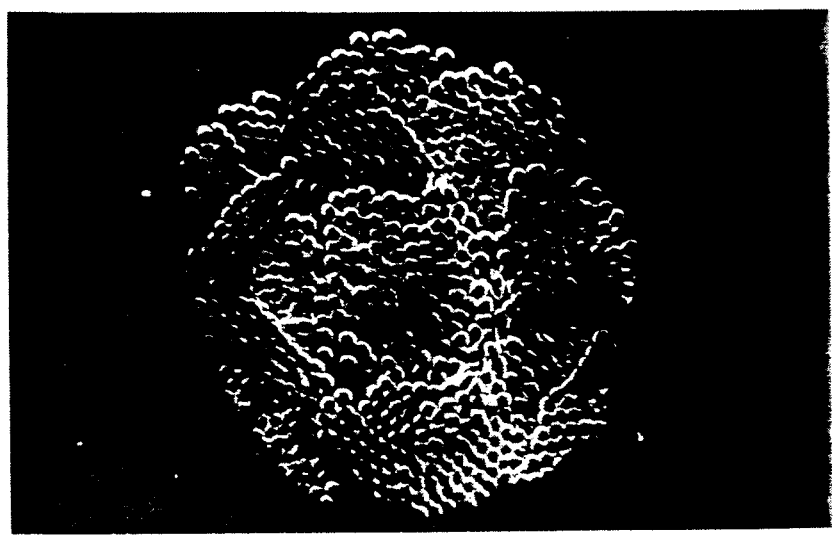
Figure 9:
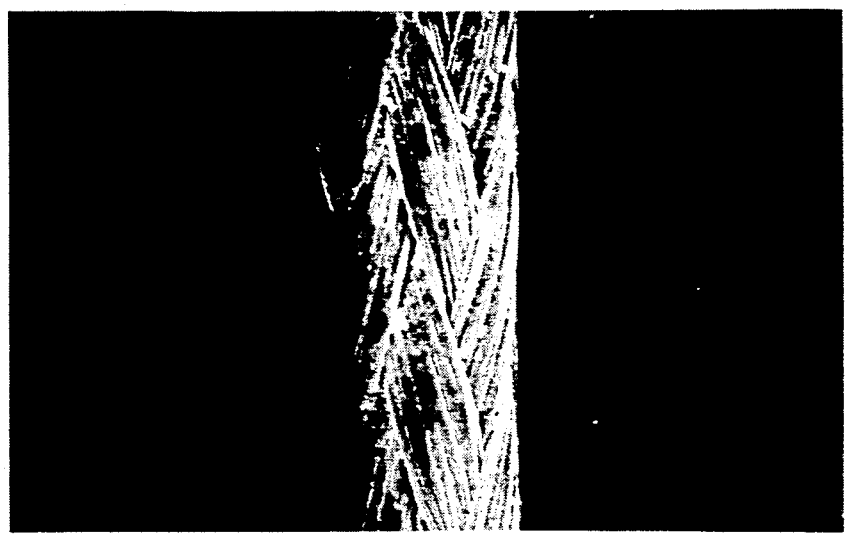
Figure 10:
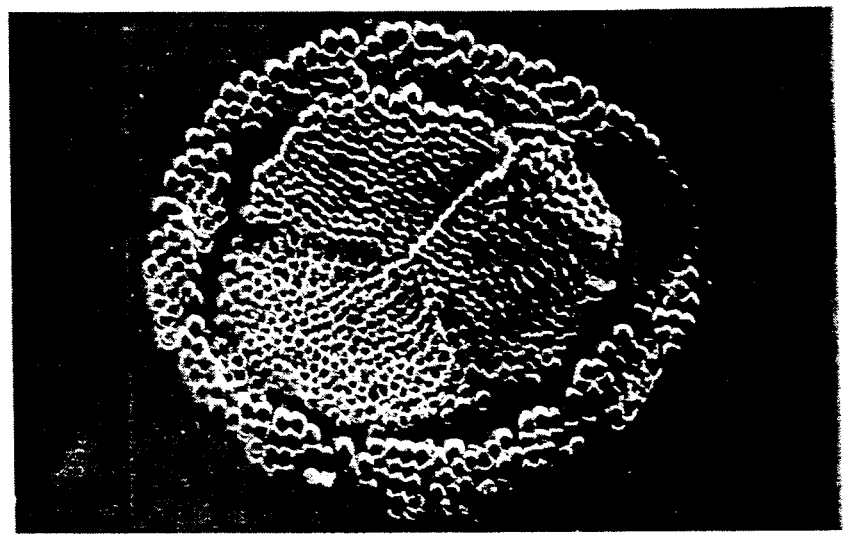
Figure 11:
Figure 12:
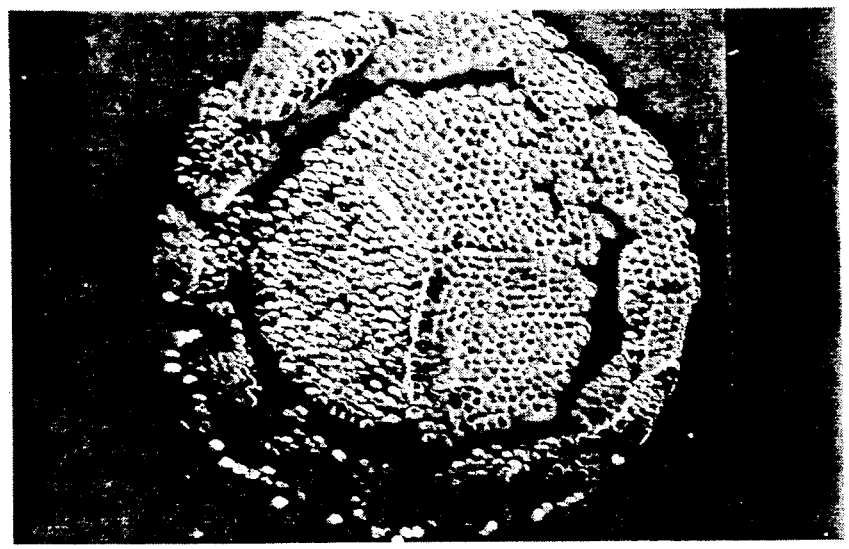
Figure 13:

These data clearly show that the smoother surface of the braided sutures fabricated in accordance with this invention provides smoother, more resistance-free passage of the suture through tissue thereby resulting in lower tissue drag and chatter. High drag forces make it more difficult for the surgeon to align tissue neatly and increase the time to complete the closure. A visual comparison of the suture of Comparative Example 10 and those of Examples 13 and 14 of this invention are consistent with the tissue drag observations set forth above. Thus, it is evident from a visual comparison of the SEM photomicrographs of FIGS. 8 and 9 (suture of Comparison Example 10 shown in cross-sectional view at 150x and linear view at 70x, respectively) with those of FIGS. 10 and 11 (suture of Example 13 shown in cross-section at 150x and linear view at 70x, respectively) and FIGS. 12 and 13 (suture of Example 14 shown in cross-section at 150x and linear view at 70x, respectively) that the external surfaces of the sutures of the present invention, i.e., those of Examples 13 and 14, are perceptibly smoother than the surfaces of the suture of Comparison Example 10.

EXAMPLE 16

Figure 14:
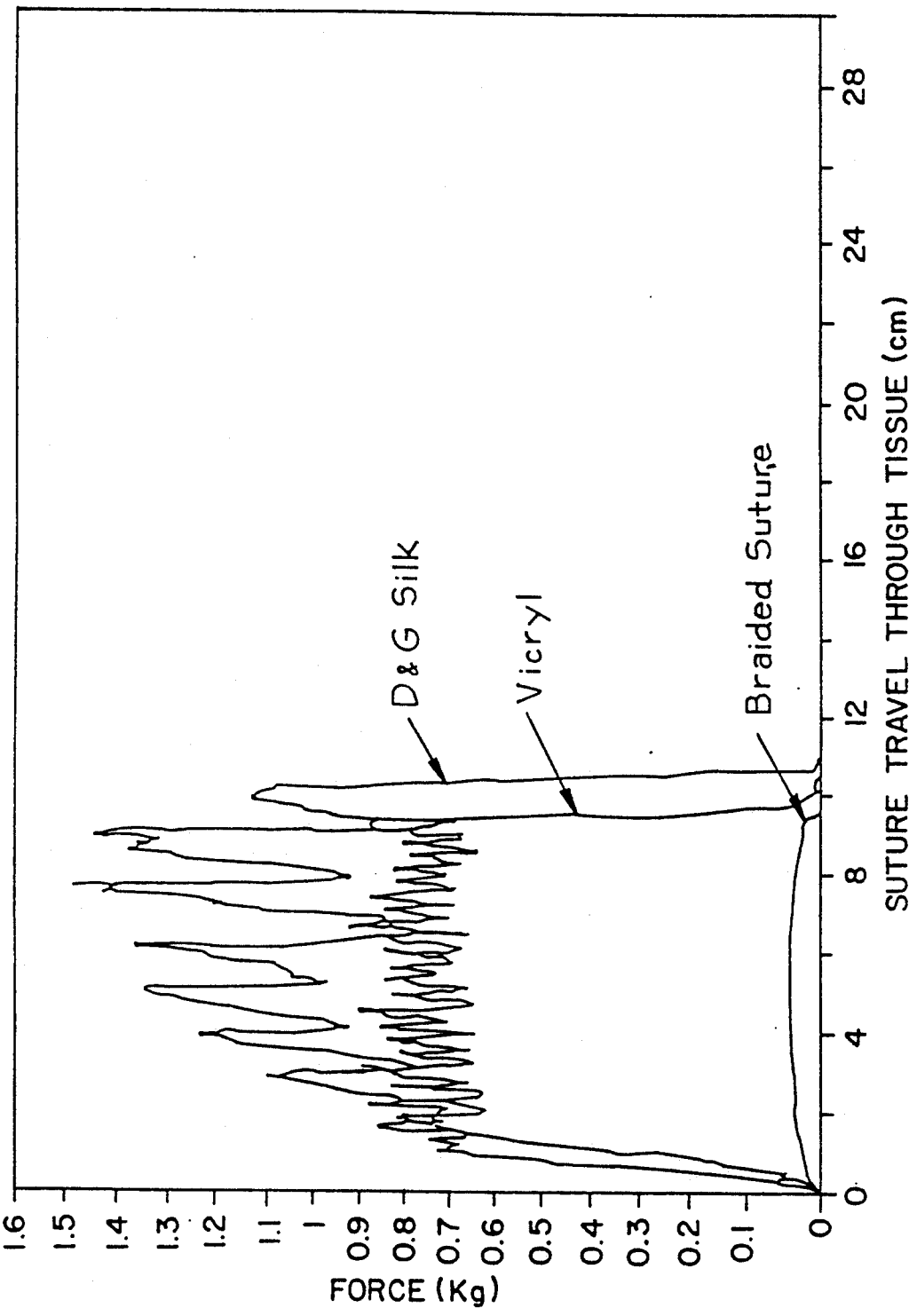

A size 2/0 filled, coated braided suture constructed in accordance with the criteria set forth, supra, was compared with a size 2/0 coated braided silk suture of Davis & Geck, Inc. ("D & G Silk") and a size 2/0 coated braided absorbable suture of Ethicon, Inc. ("Vicryl") for tissue drag. The tissue drag profiles of the three sutures appear in FIG. 14 as the plot of force (kg) required to pull each suture through animal fascia tissue through a distance of somewhat greater than 10 cm. As the graphically represented data show, the braided suture constructed in accordance with the principles of this invention exhibited a dramatically reduced level of tissue drag compared with that of the two standard sutures.

EXAMPLE 17

This example is illustrative of a size 2/0 braided glycolide-lactide copolymer suture component 30 filled with a wound healing enhancing amount of an HGF- and carrier/storage stabilizing agent-containing filling composition.

A solution of glycerol (278 gm), calcium lactate (43 gm) and sterile water (370 gm) is prepared. Human Growth Factor hEGF-51 (152.6 mg) (Creative Biomolecules, Inc., Hopkinton, Mass.) was dissolved volumetrically to 25 ml with the above solution to provide a braided suture filling composition. The composition was placed in the syringe pump of a suture coating apparatus. The syringe pump was set to provide the filling composition at a constant rate and the suture speed was adjusted to apply 17 ml of filling composition to 200 meters of braid. The target concentration of HGF on the braid is 0.52 mg hEGF/meter or approximately 1.8 mg hEFG/gram of braid. After filling, the braid was immediately passed through a 50° drying column. After filling, the spooled braid was removed to a small chamber and stored under a flowing dry nitrogen atmosphere to remove the water from the solution.

While the foregoing description contains many specifics, these specifics should not be construed as limitations on the scope of the invention, but merely as exemplifications of preferred embodiments thereof. Those skilled in the art will envision many other possible variations that are within the scope and spirit of the invention as defined by the accompanying claims.

What is claimed is:

1. A method of attaching a surgical needle to a braided suture to provide a combined surgical needle-braided suture device which comprises:
   a) providing a surgical needle possessing a shank end of reduced diameter;
   b) providing a braided suture possessing a tip region for attachment to the shank end of the needle;
   c) placing a shrinkable tubing around the reduced diameter needle shank end and the tip region of the suture to be attach thereto; and
   d) applying energy to the shrinkable tubing to bring the tubing into engagement with the end of the needle shank and the tip region of the suture thereby providing the combined surgical needle-braided suture device;
   wherein the range for pick count, number of sheath yarns and denier of individual filaments of a sheath yarn for a given size of braided suture to be attached to the needle are related to each other as follows:

| Overall Suture Denier | Pick Count | Number of Sheath Yarns | Denier of Individual Filaments |
|---|---|---|---|
| from about 50 to about 125 | from about 50 to about 100 | from about 4 to about 16 | from about 0.2 to about 1.8 |
| greater than about 125 to about 200 | from about 50 to about 100 | from about 4 to about 16 | from about 0.2 to about 1.8 |
| greater than about 200 to about 300 | from about 50 to about 100 | from about 4 to about 16 | from about 0.2 to about 6.0 |
| greater than about 300 to about 500 | from about 50 to about 100 | from about 10 to about 20 | from about 0.2 to about 6.0 |
| greater than about 500 to about 800 | from about 50 to about 100 | from about 14 to about 20 | from about 0.2 to about 6.0 |
| greater than about 800 to about 1200 | from about 50 to about 100 | from about 16 to about 32 | from about 0.2 to about 6.0 |
| greater than about 1200 to about 2000 | from about 50 to about 100 | from about 20 to about 36 | from about 0.2 to about 6.0 |
| greater than about 2000 to about 4000 | from about 50 to about 100 | from about 20 to about 36 | from about 0.2 to about 6.0. |

2. The method of claim 1 wherein the needle is manufactured from a material selected from the group consisting of Series 300 stainless steels, Series 400 stainless steels and an alloy comprising from about 6 to about 25 weight percent iron, from about 18 to about 40 weight percent nickel, from about 6 to about 12 weight percent molybdenium and from about 5 to about 25 weight percent chromium, the balance of the alloy being cobalt.

3. The method of claim 1 wherein the shrinkable tubing is manufactured from a shrinkable plastic material.

4. The method of claim 3 wherein the shrinkable plastic material is a polyvinylidene fluoride material.

5. The method of claim 1 wherein the tip region of the suture possesses an adhesive or resinous coating.

6. The method of claim 1 wherein the shrinkable tubing is sequentially placed around the shank end of the needle and the tip region of the suture and energy is applied to the shrinkable tubing after each placement.

7. The method of claim 1 wherein for a given overall suture denier, the range of pick count, number of sheath yarns and denier of individual filaments comprising a sheath yarn for a given size of braided suture to be attached to the needle are related to each other as follows:

| Overall Suture Denier | Pick Count | Number of Sheath Yarns | Denier of Individual Filaments |
|---|---|---|---|
| from about 50 to about 125 | from about 55 to about 80 | from about 6 to about 14 | from about 1.0 to about 1.8 |
| greater than about 125 to about 200 | from about 55 to about 80 | from about 6 to about 14 | from about 1.0 to about 1.8 |
| greater than about 200 to about 300 | from about 55 to about 80 | from about 6 to about 14 | from about 1.0 to about 1.8 |
| greater than about 300 to about 500 | from about 55 to about 80 | from about 12 to about 14 | from about 1.0 to about 1.8 |
| greater than about 500 to about 800 | from about 55 to about 80 | from about 14 to about 18 | from about 1.0 to about 1.8 |
| greater than about 800 to about 1200 | from about 55 to about 80 | from about 20 to about 30 | from about 1.0 to about 1.8 |
| greater than about 1200 to | from about 55 to about 80 | from about 24 to about 34 | from about 1.0 to about 1.8 |

-continued

| Overall Suture Denier | Pick Count | Number of Sheath Yarns | Denier of Individual Filaments |
|---|---|---|---|
| about 2000 greater than about 2000 to about 4000. | from about 55 to about 80 | from about 24 to about 34 | from about 1.0 to about 1.8 |

8. The method of claim 1 wherein the braided suture possesses a core.

9. The method of claim 8 wherein the overall suture denier and core denier for a given size of braided suture are related to each other as follows:

| Overall Suture Denier | Denier of Core |
|---|---|
| greater than about 125 to about 200 | from about 20 to about 80 |
| greater than about 200 to about 300 | from about 30 to about 100 |
| greater than about 300 to about 500 | from about 80 to about 150 |
| greater than about 500 to about 800 | from about 150 to about 300 |
| greater than about 800 to about 1200 | from about 250 to about 700 |
| greater than about 1200 to about 2000 | from about 400 to about 1200 |
| greater than about 2000 to about 4000. | from about 800 to about 2400 |

10. A combined surgical needle-braided suture device which comprises:
   a) a surgical needle possessing a shank end of reduced diameter;
   b) a braided suture possessing a tip region for attachment to the shank end of the needle; and
   c) a tubing engaging the shank end of the needle and the tip region of the suture, the tubing being fabricated from a material which undergoes contraction upon application of energy thereto;
   wherein for a given overall suture denier, the range of pick count, number of sheath yarns and denier of individual filaments of a sheath yarn for a given size of braided suture are related to each other as follows:

| Overall Suture Denier | Pick Count | Number of Sheath Yarns | Denier of Individual Filaments |
|---|---|---|---|
| from about 50 to about 125 | from about 50 to about 100 | from about 4 to about 16 | from about 0.2 to about 1.8 |
| greater than about 125 to about 200 | from about 50 to about 100 | from about 4 to about 16 | from about 0.2 to about 1.8 |
| greater than about 200 to about 300 | from about 50 to about 100 | from about 4 to about 16 | from about 0.2 to about 6.0 |
| greater than about 300 to about 500 | from about 50 to about 100 | from about 10 to about 20 | from about 0.2 to about 6.0 |
| greater than about 500 to about 800 | from about 50 to about 100 | from about 14 to about 20 | from about 0.2 to about 6.0 |
| greater than 800 to about 1200 | from about 50 to about 100 | from about 16 to about 32 | from about 0.2 to about 6.0 |
| greater than about 1200 to about 2000 | from about 50 to about 100 | from about 20 to about 36 | from about 0.2 to about 6.0 |
| greater than about 2000 | from about 50 to about 100 | from about 20 to about 36 | from about 0.2 to about |

-continued

| Overall Suture Denier | Pick Count | Number of Sheath Yarns | Denier of Individual Filaments |
|---|---|---|---|
| about 4000 | | | 6.0. |

11. The combined surgical needle-braided suture device of claim 10 wherein said needle is straight or curved and is manufactured from a material selected from the group consisting of Series 300 stainless steels, Series 400 stainless steels and an alloy comprising from about 6 to about 25 weight percent iron, from about 18 to about 40 weight percent nickel, from about 6 to about 12 weight percent molybdenium and from about 5 to about 25 weight percent chromium, the balance of the alloy being cobalt.

12. The combined surgical needle-braided suture device of claim 10 wherein said tubing is manufactured from a shrinkable plastic material.

13. The combined surgical needle-braided suture device of claim 12 wherein said shrinkable plastic material is a polyvinylidene fluoride material.

14. The combined surgical needle-braided suture device of claim 10 wherein the pull-out force for the device is as defined for standard needle attachment.

15. The combined surgical needle-braided suture device of claim 10 wherein the pull-out force for the device is as defined for removable needle attachment.

16. The combined surgical needle-braided suture device of claim 10 wherein the tip region of the braided suture is tipped with an adhesive or resinous coating.

17. The combined surgical needle-braided suture device of claim 10 wherein for a given overall suture denier, the range of pick count, number of sheath yarns and denier of individual filaments comprising a sheath yarn for a given size of braided suture are related to each other as follows:

| Overall Suture Denier | Pick Count | Number of Sheath Yarns | Denier of Individual Filaments |
|---|---|---|---|
| from about 50 to about 125 | from about 55 to about 80 | from about 6 to about 14 | from about 1.0 to about 1.8 |
| greater than about 125 to about 200 | from about 55 to about 80 | from about 6 to about 14 | from about 1.0 to about 1.8 |
| greater than about 200 to about 300 | from about 55 to about 80 | from about 6 to about 14 | from about 1.0 to about 1.8 |
| greater than about 300 to about 500 | from about 55 to about 80 | from about 12 to about 14 | from about 1.0 to about 1.8 |
| greater than about 500 to about 800 | from about 55 to about 80 | from about 14 to about 18 | from about 1.0 to about 1.8 |
| greater than about 800 to about 1200 | from about 55 to about 80 | from about 20 to about 30 | from about 1.0 to about 1.8 |
| greater than about 1200 to about 2000 | from about 55 to about 80 | from about 24 to about 34 | from about 1.0 to about 1.8 |
| greater than about 2000 to about 4000. | from about 55 to about 80 | from about 24 to about 34 | from about 1.0 to about 1.8 |

18. The combined surgical needle-braided suture device of claim 17 wherein the braided suture possesses a core.

19. The combined surgical needle-braided suture device of claim 10 wherein the braided suture possesses a core.

20. The combined surgical needle-braided suture device of claim 10 wherein the braided suture possesses a core.

21. The combined surgical needle-braided suture device of claim 10 wherein the braided suture is fabricated from a non-absorbable material.

22. The combined surgical needle-braided suture device of claim 21 wherein the non-absorbable material is cotton, silk, polyamide or polyolefin.

23. The combined surgical needle-braided suture device of claim 10 wherein the individual filaments of the braided suture are fabricated from a bio-absorbable polymer.

24. The combined surgical needle-braided suture device of claim 23 wherein the individual filaments of the braided suture are fabricated from a polymer derived at least in part from one or more monomers selected from the group consisting of glycolic acid, glycolide, lactic acid and lactide.

25. The combined surgical needle-braided suture device of claim 10 wherein the braided suture is fabricated from a material which is susceptible to hydrolysis, the suture possessing a storage stabilizing amount of at least one water soluble, liquid polyhydroxy compound and/or ester thereof as storage stabilizing agent.

26. The combined surgical needle-braided suture device of claim 25 wherein the water soluble, liquid polyhydroxy compound is glycerol.

27. The combined surgical needle-braided suture device of claim 26 wherein the glycerol is admixed with calcium lactate.

28. The combined surgical needle-braided suture device of claim 25 wherein the water soluble, liquid polyhydroxy compound and/or ester thereof is admixed with a thickener.

29. The combined surgical needle-braided suture device of claim 28 wherein the thickener is a saturated aliphatic hydroxycarboxylic acid or salt of the general formula

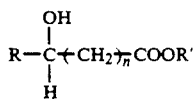

wherein R is hydrogen or a methyl group, R' is hydrogen or a metal selected from the group consisting of alkali metal and alkaline earth metal and n is 0 or 1 and hydrates thereof.

30. The combined surgical needle-braided suture device of claim 29 wherein the saturated aliphatic hydroxycarboxylic acid salt is calcium lactate.

31. The combined surgical needle-braided suture device of claim 25 wherein the braided suture is surface-coated with a composition which enhances the surface lubricity and/or knot tie-down performance of the suture.

32. The combined surgical needle-braided suture device of claim 31 wherein the composition is a bioabsorbable coating composition obtained by copolymerizing a polyether glycol with a mixture of lactide monomer and glycolide monomer or a preformed copolymer of lactide and glycolide.

33. The combined surgical needle-braided suture device of claim 32 wherein the polyether glycol is selected from the group consisting of low molecular weight polyalkylene glycol and polyethylene oxide-polypropylene oxide copolymer.

34. The combined surgical needle-braided suture device of claim 10 wherein the braided suture is surface coated with a composition enhancing one or more functional properties of the suture.

35. The combined surgical needle-braided suture device of claim 34 wherein the braided suture is surface-coated with a composition which enhances the surface lubricity and/or knot tie-down performance of the suture.

36. The combined surgical needle-braided suture device of claim 35 wherein the composition is a bioabsorbable coating composition obtained by copolymerizing a polyether glycol with a mixture of lactide monomer and glycolide monomer or a preformed copolymer of lactide and glycolide.

37. The combined surgical needle-braided suture device of claim 36 wherein the polyether glycol is selected from the group consisting of low molecular weight polyalkylene glycol and polyethylene oxide-polypropylene oxide copolymer.

38. The combined surgical needle-braided suture device of claim 10 wherein the braided suture contains at least one medico-surgically useful substance.

39. The combined surgical needle-braided suture device of claim 38 wherein the medico-surgically useful substance is at least one Human Growth Factor.

40. The combined surgical needle-braided suture device of claim 10 wherein the braided suture is filled with a filling composition comprising a surgical wound healing enhancing amount of at least one Human Growth Factor and as carrier therefor, at least one water soluble, liquid polyhydroxy compound and/or ester thereof.

41. The combined surgical needle-braided suture device of claim 40 wherein the carrier is glycerol.

42. The combined surgical needle-braided suture device of claim 40 wherein the filling composition includes a thickener.

43. The combined surgical needle-braided suture device of claim 42 wherein the thickener is a saturated aliphatic hydroxycarboxylic acid or salt of the general formula

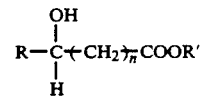

wherein R is hydrogen or a methyl group, R' is hydrogen or a metal selected from the group consisting of alkali metal and alkaline earth metal and n is 0 or 1 and hydrates thereof.

44. The combined surgical needle-braided suture device of claim 43 wherein the thickener is calcium lactate.

45. The combined surgical needle-braided suture device of claim 42 wherein the carrier is glycerol and the thickener is calcium lactate.

46. The combined surgical needle-braided suture device of claim 40 wherein the braided suture is fabricated from a material which is susceptible to hydrolysis, the carrier being present in the filling composition in an amount sufficient to stabilize the suture against excessive hydrolysis during storage.

* * * * *